(12) United States Patent
Glaug et al.

(10) Patent No.: US 11,406,543 B2
(45) Date of Patent: Aug. 9, 2022

(54) MULTIFUNCTIONAL DISPOSABLE ABSORBENT ARTICLE

(71) Applicant: Hill-Rom Services, Inc., Batesville, IN (US)

(72) Inventors: Frank Glaug, Eau Claire, WI (US); Ricardo Borrero, Eau Claire, WI (US); Mitch Simington, Eau Claire, WI (US)

(73) Assignee: Hill-Rom Services, Inc., Batesville, IN (US)

( * ) Notice: Subject to any disclaimer, the term of this patent is extended or adjusted under 35 U.S.C. 154(b) by 463 days.

(21) Appl. No.: 16/340,860

(22) PCT Filed: Oct. 11, 2017

(86) PCT No.: PCT/EP2017/075886
§ 371 (c)(1),
(2) Date: Apr. 10, 2019

(87) PCT Pub. No.: WO2018/069368
PCT Pub. Date: Apr. 19, 2018

(65) Prior Publication Data
US 2019/0262195 A1    Aug. 29, 2019

Related U.S. Application Data

(60) Provisional application No. 62/407,161, filed on Oct. 12, 2016, provisional application No. 62/407,152, filed on Oct. 12, 2016.

(51) Int. Cl.
*A61F 13/15*     (2006.01)
*A61F 13/511*    (2006.01)
*A61F 13/513*    (2006.01)

(52) U.S. Cl.
CPC ...... *A61F 13/51104* (2013.01); *A61F 13/513* (2013.01); *A61F 2013/15048* (2013.01);
(Continued)

(58) Field of Classification Search
CPC .......... A61F 13/51104; A61F 13/51108; A61F 13/513; A61F 13/51305;
(Continued)

(56) References Cited

U.S. PATENT DOCUMENTS 4,021,870 A * 5/1977 Walters .................. A61F 5/485
                                                          5/495
4,961,982 A    10/1990 Taylor
(Continued)

FOREIGN PATENT DOCUMENTS

GB    2023067 A    12/1979
GB    2254786 A    10/1992
(Continued)

OTHER PUBLICATIONS

"International Application Serial No. PCT/EP2017/075886, International Search Report dated Dec. 11, 2017", (Dec. 11, 2017), 5 pgs.
(Continued)

*Primary Examiner* — Catharine L Anderson
(74) *Attorney, Agent, or Firm* — Barnes & Thornburg LLP

(57) ABSTRACT

The present invention is a multifunctional disposable absorbent article providing numerous features including, in addition to containment and absorption of bodily fluid secretions, improved feel, dryness, and comfort upon a person's skin, odor control and anti-microbial properties, and sufficient strength to support lifting and transferring of a person.

19 Claims, 5 Drawing Sheets

(52) U.S. Cl.
CPC ............... *A61F 2013/15056* (2013.01); *A61F 2013/15154* (2013.01)

(58) Field of Classification Search
CPC .. A61F 2013/15292; A61F 2013/15552; A61F 2013/00404; A61F 2013/15048; A61F 2013/15056; A61F 2013/15073; A61F 2013/15154
See application file for complete search history.

(56) References Cited

U.S. PATENT DOCUMENTS

| | | | | |
|---|---|---|---|---|
| 6,171,682 | B1 * | 1/2001 | Raidel | A61F 13/15203 428/182 |
| 6,362,391 | B1 * | 3/2002 | Mizutani | A61F 13/51108 604/379 |
| 6,375,644 | B2 * | 4/2002 | Mizutani | A61F 13/51104 604/385.01 |
| 6,436,081 | B1 * | 8/2002 | Wada | A61F 13/4752 604/385.01 |
| 6,648,869 | B1 * | 11/2003 | Gillies | A61F 13/51104 604/385.101 |
| 6,802,932 | B2 * | 10/2004 | Kudo | A61F 13/15699 156/322 |
| 6,926,948 | B2 * | 8/2005 | Toyoshima | A61F 13/51108 428/172 |
| 9,005,728 | B2 * | 4/2015 | Johnston | B32B 7/12 428/317.1 |
| 2008/0306462 | A1 * | 12/2008 | Bruckner | A61F 13/53 604/365 |
| 2009/0312684 | A1 * | 12/2009 | Leonard | D03D 15/37 602/44 |
| 2015/0210038 | A1 * | 7/2015 | Ichikawa | B32B 7/04 428/219 |
| 2015/0230997 | A1 * | 8/2015 | Suzuki | A61F 13/49413 604/385.28 |

FOREIGN PATENT DOCUMENTS

| | | | | |
|---|---|---|---|---|
| WO | WO-9111161 A1 * | 8/1991 | ....... | A61F 13/53747 |
| WO | WO-9600545 A1 | 1/1996 | | |

OTHER PUBLICATIONS

"International Application Serial No. PCT/EP2017/075886, Written Opinion dated Dec. 11, 2017", (Dec. 11, 2017), 9 pgs.

* cited by examiner

Top Sheet: 10 gsm SBPP
Absorbent Core: 135 gsm Airlaid
Adhesive Shim Pattern: 1mm x 1mm Top Sheet: 17 gsm SBPP
Absorbent Core: 175 gsm Airlaid
Adhesive Shim Pattern: 1mm x 4mm

MULTIFUNCTIONAL DISPOSABLE ABSORBENT ARTICLE

PRIORITY APPLICATIONS

This application is a U.S. national phase of PCT/EP2017/075886, filed on Oct. 11, 2017, which claims priority to U.S. Provisional Application No. 62/407,161, filed Oct. 12, 2016, and U.S. Provisional Application No. 62/407,152, also filed on Oct. 12, 2016, and each of which is hereby incorporated by reference herein.

FIELD

The present disclosure relates generally to absorbent products, and, more particularly, to a multifunctional disposable absorbent article providing numerous features including, in addition to containment and absorption of bodily fluid secretions, improved feel, dryness, and comfort against human skin, odor control and anti-microbial properties, and sufficient strength to support lifting and transferring of a person.

BACKGROUND

There are several types of commercially available products for the absorption of bodily fluids. Such absorbent products are available in different types, designs, and dimensions, each one having one or more unique features. For example, training pants, baby diapers, adult diapers, and incontinence guards are products designed for the containment of urine and excrement. There are other types of disposable absorbent articles, such as feminine hygiene products (e.g., heavy and light incontinence pads, pantyliners, etc.) that are designed to contain and absorb urine and/or menses by female wearers. Another type of absorbent article includes underpads configured to absorb and collect body fluid discharge from a person who may be generally confined to a bed or chair, or may otherwise be immobilized.

Currently known absorbent products typically include a top sheet facing the body of the wearer, a back sheet facing a garment of the wearer or a bed or chair (or other object) upon which the person is placed, and an absorbent core sandwiched between the top sheet and back sheet. While these types of absorbent articles may collect body fluid discharge as intended, many of these products tend to leak the secreted fluids, which may lead to discomfort for the wearer and/or the caretaker. For example, bed sores, also known as pressure ulcers or decubitus ulcers, are prevalent among people who are bed-ridden or otherwise immobilized. Skin ulcers can be caused by pressure exerted on the skin and soft tissues (e.g., the individual's body weight resting against a hard surface such as a bed or chair) and are exacerbated when the skin is also exposed to moisture (e.g., due to incontinence) and/or friction, heat, sweat, and shear forces, for example caused by moving or repositioning a bed-ridden patient. Elderly nursing home residents are particularly vulnerable to pressure ulcers since they are frequently bed-ridden and incontinent.

Current commercially available absorbent underpads are generally insufficient for use with bedridden or immobile persons. For example, some currently available underpads generally lack adequate fluid retention, such that fluid may leak from the underpad. Furthermore, the top sheet of current underpads have become increasingly thin having relatively lower basis weights (e.g., 7-10 grams per square meter (gsm)). Accordingly, current underpads, which lack sufficient absorbency/retention and strength, thereby leading to leaks and tears, will likely exacerbate the formation of bed sores, which may subsequently lead to infection and possible death if left untreated. Since bed ulcers can be persistent and heal slowly, treating pressure ulcers (once formed) is thus expensive, so there is a significant need to minimize a patient's exposure to conditions which would cause such ulcers.

SUMMARY

The present invention provides a multifunctional disposable absorbent article providing numerous features, in addition to containment and absorption of bodily fluid secretions. More specifically, the present invention provides a disposable underpad including at least a majority, if not all, key functional features of any absorbent product assembled into a single product design. For example, the absorbent underpad is designed in such a manner so as to: maintain skin dryness by sufficiently absorbing moisture while preventing leakage to a person's skin or underlying garment or bed; allow adequate air circulation at the surface of the person's skin to prevent heat buildup; and provide sufficient strength to support lifting and transferring or repositioning of a person, even when the underpad is wet. The underpad may further provide improved feel and softness against the person's skin, as well as odor control and anti-microbial properties.

While the multifunctional underpad design of the present disclosure may be used in a variety of different absorbent products, such as, for example, training pants, baby diapers, adult diapers, incontinence guards, wound care, and feminine hygiene article, the multifunctional underpad may be particularly beneficial for bed-ridden or immobilized persons who are incontinent or have other moisture management issues. The underpad of the present disclosure is designed in such a way so as to provide numerous key features that, in the aggregate, decrease the risk of bed sore formation and maintain a person's skin health or promote healing thereof. For example, the underpad of the present disclosure provides improved Rate of Acquisition (ROA), improved softness and resiliency, improved insulation against free fluid migration and rewet when the pad is in a wet state, adequate air circulation between the pad and a person's skin, increased tensile strength to improve durability and provide sufficient strength for lifting and transferring/repositioning a person, odor control properties, anti-microbial properties, and pH control.

Accordingly, the multifunctional underpad of the present disclosure provides numerous advantages over currently available absorbent products in that all, or most all, key and desired features are assembled into a single product design. Accordingly, the multifunctional underpad is able to efficiently manage moisture and help maintain skin integrity over time with added patient comfort, thereby cutting down on overall costs that would otherwise be associated with the preventative maintenance and/or ongoing treatment of bed sores incurred with conventional underpads.

Accordingly, the multifunctional underpad of the present disclosure provides numerous advantages over currently available absorbent products in that all, or most all, key and desired features are assembled into a single product design. Accordingly, the multifunctional underpad is able to efficiently manage moisture and help maintain skin integrity over time with added patient comfort, thereby cutting down on overall costs that would otherwise be associated with the preventative maintenance and/or ongoing treatment of bed sores incurred with conventional underpads.

In one aspect, the present disclosure provides a disposable absorbent article having a first layer configured to engage a subject's skin and a second layer coupled to the first layer and having at least one absorbent material for absorbing a fluid passing through the first layer. The first layer includes a breathable and fluid permeable material configured to absorb fluid and provide a degree of compression against the subject's skin. The first and second layers are coupled to one another via a plurality of adhesive bonds. As a result of a particular pattern of adhesive bonds, the first layer includes a plurality of longitudinal peaks and valleys adjacent to one another and extending along a length of the first layer. The plurality of peaks and valleys are configured to distribute fluid along the first layer and into the second layer in a direction corresponding to the orientation of the peaks and valleys.

For example, in some embodiments, the adhesive bonds are arranged in a substantially parallel pattern relative to one another along a length of the first and second layers such that the plurality of peaks and valleys are substantially parallel to one another. Accordingly, the plurality of peaks and valleys may generally be configured to distribute fluid along the first layer and into the second layer in a substantially longitudinal direction corresponding to the longitudinal orientation of the peaks and valleys. Accordingly, in an absorbent article having a rectangular shape, it may be desirable to arrange the peaks and valleys in a direction associated with the length of the article, as there is much more area to work with and the fluid can be distributed along the length, as opposed to the width, of the article, thereby preventing or reducing the risk of fluid leaking towards the edges. In addition to improving fluid distribution, the plurality of longitudinal peaks and valleys may generally improve at least one of softness, rate of acquisition (ROA), efficiency of use of absorbent surface area (which can provide significant cost savings), and a combination thereof. It should be noted that, in other embodiments, the peaks and valleys may be arranged in a various patterns and need not be limited to a longitudinal pattern. For example, in some embodiments, the peaks and valleys may be oriented in a substantially horizontal direction or a substantially diagonal direction relative to the first and second layers. In another example, the peaks and valleys may include a curved length, such as a serpentine pattern or the like, or the peaks and valleys may include a non-uniform shape and may vary along their length. Yet still, in some embodiments, different portions of the first layer may include different patterns of peaks and valleys, such that the pattern of peaks and valleys can vary throughout the entire area of the first layer. For example, some sets of peaks and valleys may extend in a first direction and other sets of peaks and valleys may extend in a second direction different than the first direction (e.g., first set oriented in a longitudinal direction parallel with length of article and second set oriented in a horizontal direction parallel with width of article). Furthermore, in some embodiments, the peaks and valleys may be intermittently formed along the first layer in such a manner that they are not continuous. Ultimately, the peaks and valleys can be arranged (as a result of the adhesive bond pattern) in any desired pattern so as to distribute fluid in the article as a user desires.

In some embodiments, each of the plurality of adhesive bonds may be positioned from an immediately adjacent adhesive bond in the range of approximately 1 mm to 10 mm such that the plurality of peaks are spaced apart from one another via each valley. For example, in one embodiment, each of the plurality of adhesive bonds is positioned from an immediately adjacent adhesive bond by 4 mm.

In some embodiments, the first layer includes at least one of a nonwoven material, a hydrophilic or partially hydrophilic material, a nonwoven material with a zone-coated surfactant, and a nonwoven with apertured film. The first layer may also include a combination of nonwoven layers, which may be layered upon one another via an adhesive lamination, ultrasonic bond, heat seal, or a combination thereof.

In some embodiments, the absorbent article has an ROA in the range of approximately 50 to 200 seconds based on a flow-rate of 7 ml/sec. through a 1 inch inner diameter cylinder. The absorbent article may also have a rewet in the range of approximately 0.1 grams and 10.0 grams. The breathability of the absorbent article may be measured as moisture vapor transmission rate (MVTR) having a metric perm value in the range of approximately 400 g/sm/day to 10,000 g/sm/day.

In some embodiments, the first layer has a basis weight in the range of approximately 15 gsm to 45 gsm and comprises of a hydrophilic spunbond polypropylene nonwoven. However, other hydrophilic nonwovens can be used, such as thermal-bonded carded web or spunlace. These nowovens could contain a certain percentage of cotton fibers for softness.

In some embodiments, the second layer may include a nonabsorbent material combined with the absorbent material. For example, the second layer may include cellulose wood fibers, plant fibers, cotton fibers, fluff pulp, viscose rayon, and a combination thereof. The fluff pulp may provide at least one of odor control, anti-bacterial properties, pH control, and a combination thereof. In some embodiments, the absorbent material of the fluid and retention portion of the second layer comprises a superabsorbent polymer. The superabsorbent polymer may include a polymer or copolymer of sodium polyacrylate. In some embodiments, the superabsorbent polymer may provide at least one of odor control, anti-bacterial properties, pH control, and a combination thereof. Yet still, in some embodiments, the absorbent material of the fluid and retention portion of the second layer may include tissue. Additionally, or alternatively, the second layer may include an airlaid composite. Additionally, or alternatively, the second layer may include a pulpless absorbent material.

In some embodiments, the absorbent article may include a third layer coupled to the second layer and separated from the first layer via at least the second layer, wherein the third layer includes at least a fluid impervious material. In some embodiments, the third layer may include a breathable micro-porous poly film. In some embodiments, the third layer may include a breathable SMS (Spunbond/Meltblown/Spunbond) nonwoven material. The SMS nonwoven material may include a slot coated adhesive.

In some embodiments, the absorbent article may further include a fourth layer coupled to the third layer and separated from the first and second layers via at least the third layer, the fourth layer having a breathable material. In some embodiments, the fourth layer may include a nonwoven material. For example, the fourth layer may include a SBPP (Spunbond Polypropylene) material or a SMS nonwoven material. In some embodiments, the nonwoven material of the fourth layer may include a carded web or spunlace material.

Yet further still, the absorbent article may include a fifth layer coupled to the fourth layer and separated from the first, second, and third layers via at least the fourth layer. The fifth layer may generally include a fastening mechanism to allow the absorbent article to be releasably coupled to an object. For example, the fifth layer may include a fastening mechanism to allow the absorbent article to be releasably coupled to clothing, bed linens, or objects (e.g., furniture) upon which a person will be positioned, so as to prevent undesired movement or shifting of the absorbent article.

The fastening mechanism may include micro-hooks or pressure-sensitive adhesive with release paper. The micro-hooks may be configured to releasably attach the article to cloth-like materials (mostly woven fabrics), such as bed sheets, fabric couch or chair surfaces, fabric car seats, fabric cushion pads, etc. and the pressure sensitive adhesive would allow the article to attach itself to wood, plastic, glass, leather and metal surfaces (mostly non-fabric), such as chairs, benches, bleachers, wheelchairs, leather car seats, etc.

It should be noted that, in some embodiments, the absorbent article comprises only the first, second, and third layers. Accordingly, in such an embodiment, the third layer may include the fastening mechanism as described above with reference to the fifth layer. Similarly, in some embodiments in which the absorbent article includes only the first, second, third, and fourth layers, the fourth layer may include the fastening mechanism for releasably attaching the absorbent article to an object.

In another aspect, the present disclosure provides a disposable absorbent article having a first layer configured to engage a subject's skin, a second layer coupled to the first layer and having a fluid absorption and retention portion having at least one absorbent material for absorbing a fluid passing through the first layer, and a third layer coupled to the second layer and separated from the first layer via at least the second layer, the third layer having at least a fluid impervious material. The first layer has a basis weight in the range of approximately 15 gsm to 45 gsm and a tensile strength, when measured by ASTM D 882 method, in the range of approximately 25 N/25 to 80 N/25 mm in the machine direction (MD) and approximately 9 N/25 to 50 N/25 mm in the cross direction (CD). The first layer includes a material that is fluid permeable and configured to absorb fluid, provide a degree of compression against a subject's skin, and is breathable.

In some embodiments, the first layer is coupled to the second layer via a plurality of adhesive bonds. The plurality of adhesive bonds may be arranged in a substantially parallel pattern relative to one another along a length of the first and second layers. The first layer includes a plurality of longitudinal peaks and valleys adjacent and mainly parallel to one another and extending the length of the first layer, wherein the valleys are formed via the plurality of adhesive bonds coupling the first and second layers to one another.

It should be noted that, in other embodiments, the peaks and valleys may be arranged in a various patterns and need not be limited to a longitudinal pattern. For example, in some embodiments, the peaks and valleys may be oriented in a substantially horizontal direction or a substantially diagonal direction relative to the first and second layers. Yet still, in some embodiments, different portions of the first layer may include different patterns of peaks and valleys, such that the pattern of peaks and valleys can vary throughout the entire area of the first layer. For example, some sets of peaks and valleys may extend in a first direction and other sets of peaks and valleys may extend in a second direction different than the first direction (e.g., first set oriented in a longitudinal direction parallel with length of article and second set oriented in a horizontal direction parallel with width of article). Furthermore, in some embodiments, the peaks and valleys may be intermittently formed along the first layer in such a manner that they are not continuous.

Each of the plurality of adhesive bonds is positioned from an immediately adjacent adhesive bond in the range of approximately 1 mm to 4 mm, such that the peaks are spaced apart from one another via each valley. The plurality of longitudinal peaks and valleys may be configured to improve at least one of: softness, rate of acquisition (ROA), efficiency of use of absorbent surface area (which can provide significant cost savings), wicking direction of fluid flow (which can be useful in reducing leakage from the article), and a combination thereof.

In some embodiments, the first layer includes at least one of a nonwoven material, a hydrophilic or partially hydrophilic material, a nonwoven material with a zone-coated surfactant, and a nonwoven with apertured film. The first layer may also include a combination of nonwoven layers, which may be layered upon one another via an adhesive lamination, ultrasonic bond, heat seal, or a combination thereof.

In some embodiments, the absorbent article has an ROA in the range of approximately 50 to 200 seconds based on a flow-rate of 7 ml/sec through a 1 inch inner diameter cylinder. The absorbent article may also have a rewet in the range of approximately 0.1 grams and 10.0 grams. The breathability of the absorbent article may be measured as moisture vapor transmission rate (MVTR) having a metric perm value in the range of approximately 400 glsm/day to 10,000 glsm/day.

In some embodiments, the second layer may include a nonabsorbent material combined with the absorbent material. For example, the second layer may include cellulose wood fibers, plant fibers, cotton fibers, fluff pulp, viscose rayon, and a combination thereof. The fluff pulp may provide at least one of odor control, anti-bacterial properties, pH control, and a combination thereof. In some embodiments, the absorbent material of the fluid and retention portion of the second layer comprises a superabsorbent polymer. The superabsorbent polymer may include a polymer or copolymer of sodium polyacrylate. In some embodiments, the superabsorbent polymer may provide at least one of odor control, anti-bacterial properties, pH control, and a combination thereof. Yet still, in some embodiments, the absorbent material of the fluid and retention portion of the second layer may include tissue. Additionally, or alternatively, the second layer may include an airlaid composite. Additionally, or alternatively, the second layer may include a pulpless absorbent material.

In some embodiments, the third layer may include a breathable micro-porous poly film.

In some embodiments, the third layer may include a breathable SMS (Spunbond/Meltblown/Spunbond) nonwoven material. The SMS nonwoven material may include a slot coated adhesive. In some embodiments, the absorbent article may further include a fourth layer coupled to the third layer and separated from the first and second layers via at least the third layer, the fourth layer having a breathable material. In some embodiments, the fourth layer may include a nonwoven material. For example, the fourth layer may include a SBPP (Spunbond Polypropylene) material or a SMS nonwoven material. In some embodiments, the nonwoven material of the fourth layer may include a carded web. In some embodiments, the nonwoven material of the fourth layer may have a tensile strength, when measured by ASTM D 882 method, in the range of approximately 10

N/25 to 40 N/25 mm in the machine direction and approximately 5 N/25 to 25 N/25 mm in the cross direction.

Yet further still, the absorbent article may include a fifth layer coupled to the fourth layer and separated from the first, second, and third layers via at least the fourth layer. The fifth layer may generally include a fastening mechanism to allow the absorbent article to be releasably coupled to an object. For example, the fifth layer may include a fastening mechanism to allow the absorbent article to be releasably coupled to clothing, bed linens, or objects (e.g., furniture) upon which a person will be positioned, so as to prevent undesired movement or shifting of the absorbent article. The fastening mechanism may include micro-hooks or pressure-sensitive adhesive with release paper. The micro-hooks may be configured to releasably attach the article to cloth-like materials (mostly woven fabrics), such as bed sheets, fabric couch or chair surfaces, fabric car seats, fabric cushion pads, etc. and the pressure sensitive adhesive would allow the article to attach itself to wood, plastic, glass, leather and metal surfaces (mostly non-fabric), such as chairs, benches, bleachers, wheelchairs, leather car seats, etc.

It should be noted that, in some embodiments, the absorbent article comprises only the first, second, and third layers. Accordingly, in such an embodiment, the third layer may include the fastening mechanism as described above with reference to the fifth layer. Similarly, in some embodiments in which the absorbent article includes only the first, second, third, and fourth layers, the fourth layer may include the fastening mechanism for releasably attaching the absorbent article to an object.

According to an aspect of the invention, the absorbent articles has the features of any one of the following clauses:
1. An absorbent article comprising:
a first layer configured to engage a subject's skin, the first layer comprising:
a basis weight in the range of approximately 15 gsm to 45 gsm; and
a tensile strength, when measured by ASTM D 882 method, in the range of approximately 25 N/25 to 80 N/25 mm in the machine direction and approximately 9 N/25 to 50 N/25 mm in the cross direction,
wherein the first layer comprises a material that is fluid permeable and configured to absorb fluid, provide a degree of compression against a subject's skin, and is breathable;
a second layer coupled to the first layer, the second layer comprising a fluid absorption and retention portion having at least one absorbent material for absorbing a fluid passing through the first layer; and
a third layer coupled to the second layer and separated from the first layer via at least the second layer, the third layer comprising at least a fluid impervious material.
2. The absorbent article of clause 1, wherein the first layer is coupled to the second layer via a plurality of adhesive bonds.
3. The absorbent article of clause 2, wherein the plurality of adhesive bonds are arranged in a substantially parallel pattern relative to one another along a length of the first and second layers.
4. The absorbent article of clause 3, wherein the first layer comprises a plurality of longitudinal peaks and valleys adjacent and substantially parallel to one another and extending the length of the first layer, wherein the valleys are formed via the plurality of adhesive bonds coupling the first and second layers to one another.
5. The absorbent article of clause 4, wherein each of the plurality of adhesive bonds is positioned from an immediately adjacent adhesive bond in the range of approximately 1 mm to 4 mm such that the plurality of peaks are spaced apart from one another via each valley.
6. The absorbent article of clause 4, wherein the plurality of longitudinal peaks and valleys improves at least one of: softness, rate of acquisition (ROA), surface area, and a combination thereof.
7. The absorbent article of any one of the previous clauses, wherein the first layer comprises a nonwoven material.
8. The absorbent article of any one of the previous clauses, wherein the first layer comprises a hydrophilic or partially hydrophilic material.
9. The absorbent article of clause 8, wherein the first layer comprises a nonwoven material with a zone-coated surfactant.
10. The absorbent article of any one of the previous clauses, wherein the first layer comprises a nonwoven and apertured film.
11. The absorbent article of any one of the previous clauses, wherein the absorbent article has a rate of acquisition (ROA) in the range of approximately 50 to 200 seconds.
12. The absorbent article of any one of the previous clauses, wherein the absorbent article has a rewet in the range of approximately 0.1 grams and 10.0 grams.
13. The absorbent article of any one of the previous clauses, wherein the breathability is measured as moisture vapor transmission rate (MVTR) having a metric perm value in the range of approximately 400 g/sm/day to 10,000 g/sm/day.
14. The absorbent article of any one of the previous clauses, wherein the second layer comprises a nonabsorbent material combined with the absorbent material
15. The absorbent article of clause 14, wherein the second layer comprises cellulose selected from the group consisting of wood fibers, plant fibers, cotton fibers, fluff pulp and viscose rayon.
16. The absorbent article of clause 15, wherein the fluff pulp provides at least one of odor control, anti-bacterial properties, pH control, and a combination thereof.
17. The absorbent article of any one of the previous clauses, wherein the absorbent material of the fluid and retention portion of the second layer comprises a superabsorbent polymer.
18. The absorbent article of clause 17, wherein the superabsorbent polymer comprises of a polymer or copolymer of sodium polyacrylate.
19. The absorbent article of clause 17, wherein the superabsorbent polymer provides at least one of odor control, anti-bacterial properties, pH control, and a combination thereof.
20. The absorbent article of any one of the previous clauses, wherein the absorbent material of the fluid and retention portion of the second layer comprises tissue.
21. The absorbent article of any one of the previous clauses, wherein the second layer comprises an airlaid composite.
22. The absorbent article of any one of the previous clauses, wherein the second layer comprises a pulpless absorbent material.
23. The absorbent article of any one of the previous clauses, wherein the third layer comprises a breathable micro-porous poly film.
24. The absorbent article of any one of the previous clauses, wherein the third layer comprises a breathable SMS (Spunbond/Meltblown/Spunbond) nonwoven material.
25. The absorbent article of clause 24, wherein the SMS nonwoven material has a slot coated adhesive.
26. The absorbent article of any one of the previous clauses, wherein the third layer comprises one or more fastening mechanisms configured to releasably attach the absorbent article to a surface of an object.

27. The absorbent article of clause 26, wherein the fastening mechanism comprises micro-hooks.

28. The absorbent article of clause 26, wherein the fastening mechanism comprises a pressure-sensitive adhesive with release paper.

29. The absorbent article of any one of the previous clauses, further comprising a fourth layer coupled to the third layer and separated from the first and second layers via at least the third layer, the fourth layer comprising a breathable material.

30. The absorbent article of clause 29, wherein the fourth layer comprises a nonwoven material.

31. The absorbent article of clause 30, wherein the fourth layer comprises a SBPP (Spunbond Polypropylene) material.

32. The absorbent article of clause 30, wherein the fourth layer comprises a (Spunbond/Meltblown/Spunbond) nonwoven material.

33. The absorbent article of clause 30, wherein the nonwoven material of the fourth layer comprises a carded web.

34. The absorbent article of clause 30, wherein the nonwoven material of the fourth layer comprises a tensile strength, when measured by ASTM D 882 method, in the range of approximately 10 N125 to 40 N125 mm in the machine direction and approximately 5 N125 to 25 N125 mm in the cross direction.

35. The absorbent article of clause 29, wherein the fourth layer comprises one or more fastening mechanisms configured to releasably attach the absorbent article to a surface of an object.

36. The absorbent article of clause 35, wherein the fastening mechanism comprises micro-hooks.

37. The absorbent article of clause 35, wherein the fastening mechanism comprises a pressure-sensitive adhesive with release paper.

38. The absorbent article of clause 29, further comprising a fifth layer coupled to the fourth layer and separated from the first, second, and third layers via at least the fourth layer.

39. The absorbent article of clause 38, wherein the fifth layer comprises one or more fastening mechanisms configured to releasably attach the absorbent article to a surface of an object.

40. The absorbent article of clause 39, wherein the fastening mechanism comprises micro-hooks.

41. The absorbent article of clause 39, wherein the fastening mechanism comprises a pressure-sensitive adhesive with release paper.

BRIEF DESCRIPTION OF THE DRAWINGS

Features and advantages of the claimed subject matter will be apparent from the following detailed description of embodiments consistent therewith, which description should be considered with reference to the accompanying drawings.

Figure 1:
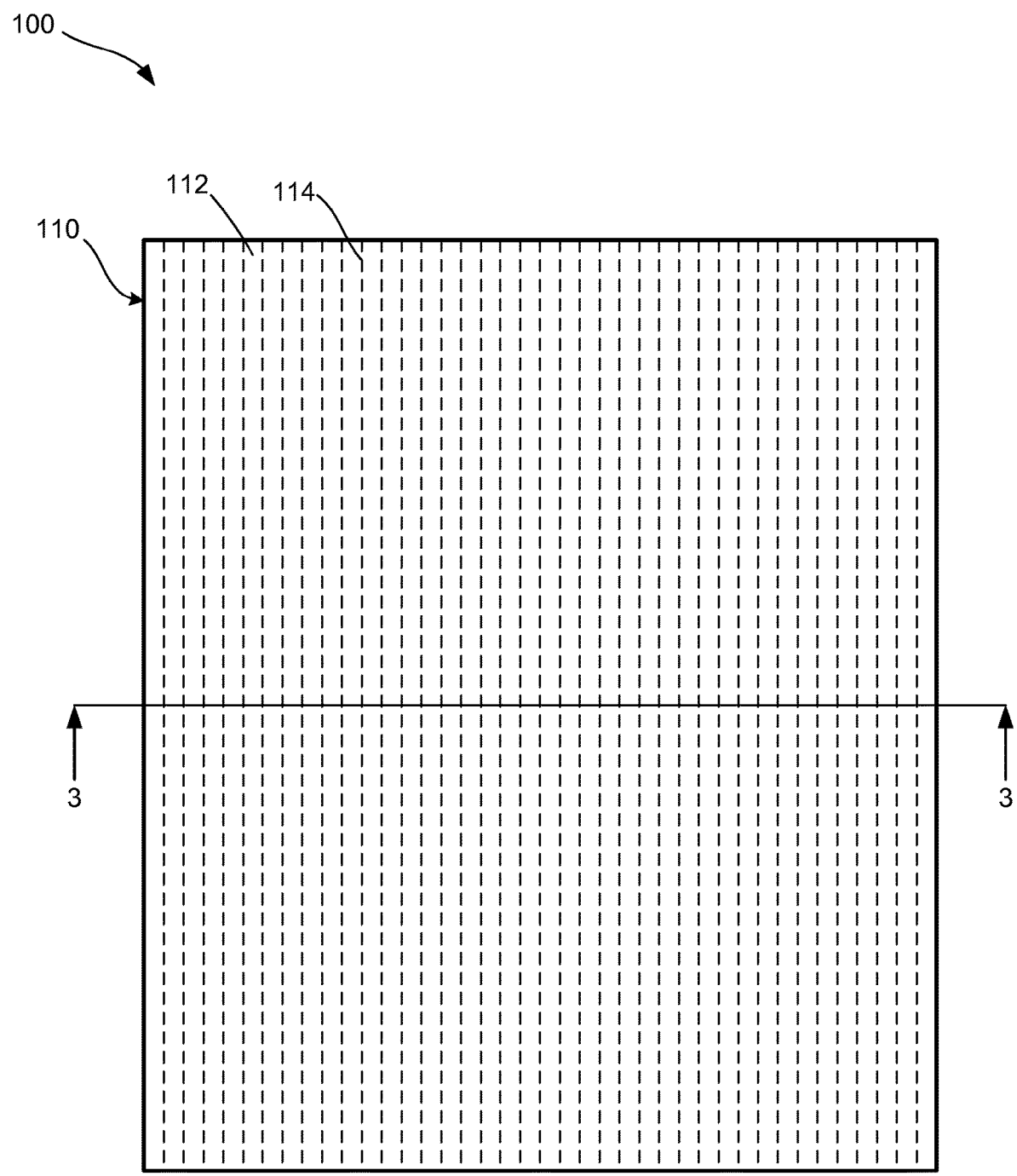
FIG. 1 is a top view of a multifunctional disposable absorbent article consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present invention provides a multifunctional disposable absorbent article providing numerous features. More specifically, in addition to providing containment and absorption of bodily fluid secretions, the multifunctional disposable absorbent article of the present disclosure provides at least a majority of, if not all, key functional features of any absorbent product assembled into a single product design. For example, the absorbent article serves as an underpad designed in such a manner so as to: maintain skin dryness by sufficiently absorbing moisture while preventing leakage to a person's skin or underlying garment or bed; allow adequate air circulation at the surface of the person's skin to prevent heat buildup; and provide sufficient strength to support lifting and transferring or repositioning of a person, even when the underpad is wet. The underpad may further provide improved feel and softness against the person's skin, as well as odor control and anti-microbial properties and pH balance.

While the multifunctional underpad design of the present disclosure may be used in a variety of different absorbent products, such as, for example, training pants, baby diapers, adult diapers, incontinence guards, wound care, and feminine hygiene article, the multifunctional underpad may be particularly beneficial for bed-ridden or immobilized persons who are incontinent or have other moisture management issues. The underpad of the present disclosure is designed in such a way so as to provide numerous key features that, in the aggregate, decrease the risk of bed sore formation and maintain a person's skin health or promote healing thereof. For example, the underpad of the present disclosure provides improved Rate of Acquisition (ROA), improved softness and resiliency, improved insulation against free fluid migration and rewet when the pad is in a wet state, adequate air circulation between the pad and a person's skin, increased tensile strength to improve durability and provide sufficient strength for lifting and transferring/repositioning a person, odor control properties, anti-microbial properties, and pH control.

Accordingly, the multifunctional underpad of the present disclosure provides numerous advantages over currently available absorbent products in that all, or most all, key and desired features are assembled into a single product design. Accordingly, the multifunctional underpad is able to efficiently manage moisture and help maintain skin integrity over time with added patient comfort, thereby cutting down on overall costs that would otherwise be associated with the preventative maintenance and/or ongoing treatment of bed sores incurred with conventional underpads.

Figure 2:
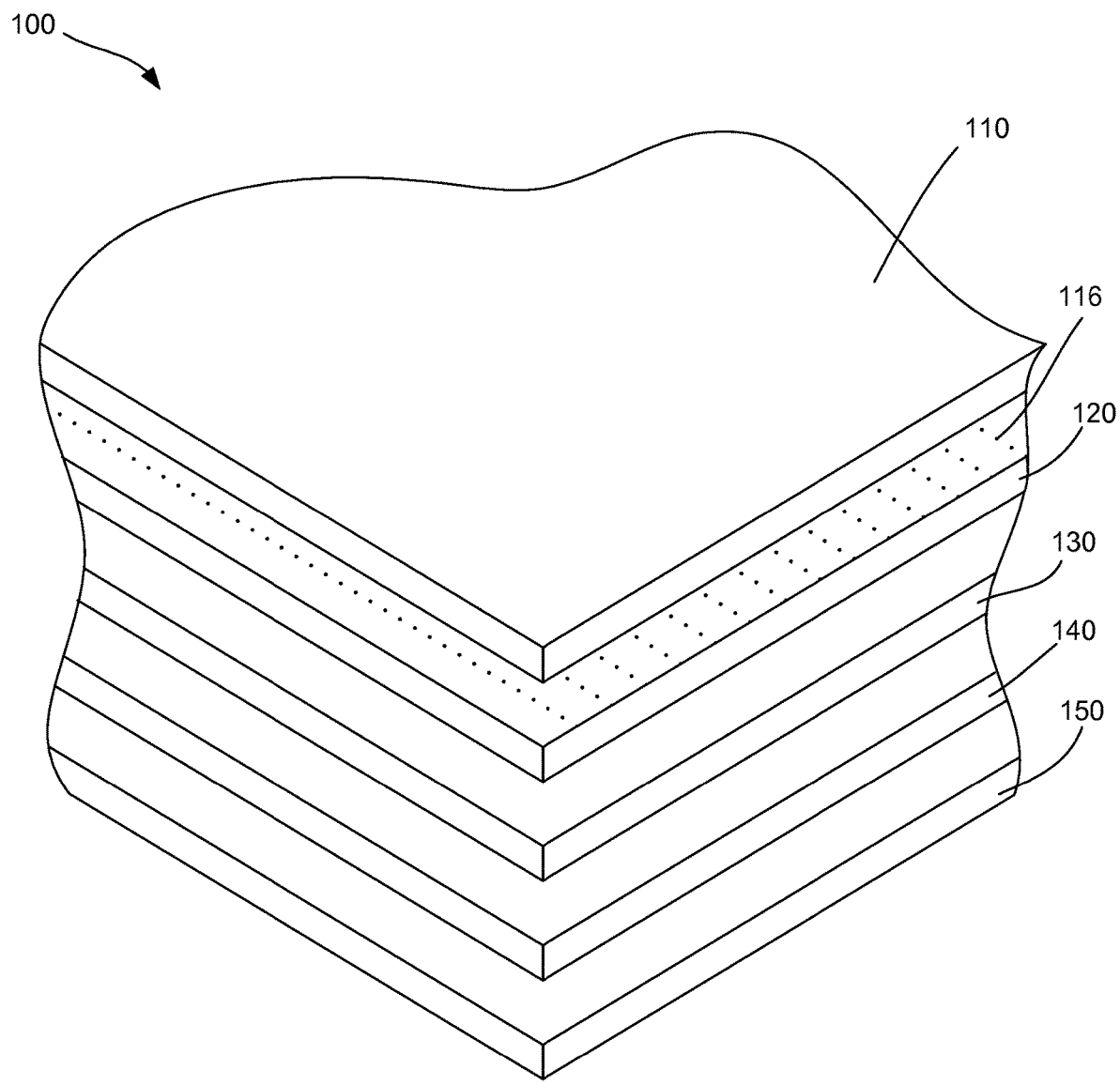
FIG. 2 is an enlarged perspective view of a portion of the absorbent article of FIG. 1 illustrating the multiple layers separated from one another.

FIG. 1 is a top view of a multifunctional disposable absorbent article 100 consistent with the present disclosure and FIG. 2 is an enlarged perspective view of a portion of the absorbent article 100 illustrating multiple layers separated from one another. The following description will refer to the absorbent article 100 as the "underpad 100". However, it should be noted that the absorbent article 100 may be included in a variety of different absorbent products, such as training pants, baby diapers, adult diapers, incontinence guards, wound care, and feminine hygiene article, and is not limited to underpads.

As shown, the underpad 100 may include at least a first layer 110, a second layer 120, and a third layer 130, wherein the second layer 120 is positioned between the first and third layers 110, 130. The first layer 110, also referred to herein as the "top sheet 110", is generally configured to engage a subject's skin and allow a fluid from the subject (i.e., human, animal, etc.) to flow therethrough, at least in a direction away from the subject's skin. The second layer 120, also referred to herein as the "absorbent core 120", includes a fluid absorption and retention portion having at least one absorbent material for absorbing a fluid passing through the top sheet 110. The third layer 130, also referred to herein as the "fluid impervious barrier 130", may generally include a fluid impervious material and is breathable, achieved by allowing water vapor and/or air to pass through the barrier 130 while preventing the passage of liquid. The barrier 130 may be configured, in cooperation with a fourth layer 140, such as another cloth-like material, to make the barrier 130 less smooth or slippery along the surface and add additional tensile strength to the underpad 100 for lifting and/or moving a person. In some embodiments, the underpad 100 may include a fifth layer 150 coupled to the fourth layer 140 and separated from the first, second, and third materials via the fourth layer 140. The fifth layer 150 may include a fastening mechanism for releasably attaching the underpad 100 to an object, such as person's garment, bedlinens, or other cloth-like materials, or furniture (e.g., bed, chair, etc.) so as to prevent undesired movement or shifting of the underpad 100. The fastening mechanism may include micro-hooks or pressure-sensitive adhesive with release paper. The micro-hooks may be configured to releasably attach the article to cloth-like materials (mostly woven fabrics), such as bed sheets, fabric couch or chair surfaces, fabric car seats, fabric cushion pads, etc. and the pressure sensitive adhesive would allow the article to attach itself to wood, plastic, glass, leather and metal surfaces (mostly non-fabric), such as chairs, benches, bleachers, wheelchairs, leather car seats, etc.

Figure 3:
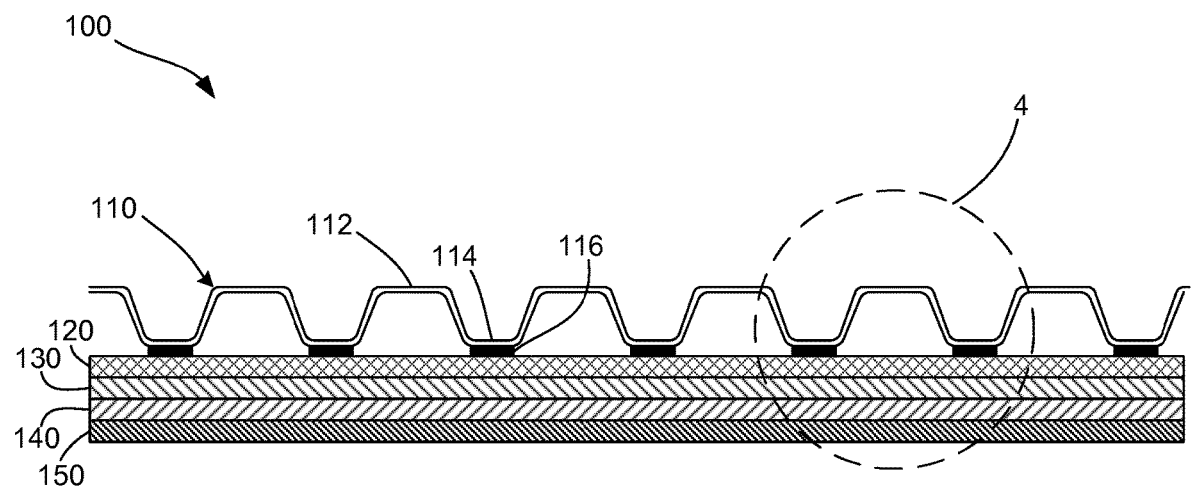
FIG. 3 is a cross-sectional view of the absorbent article taken along lines 3-3 of FIG. 1.
Figure 4:
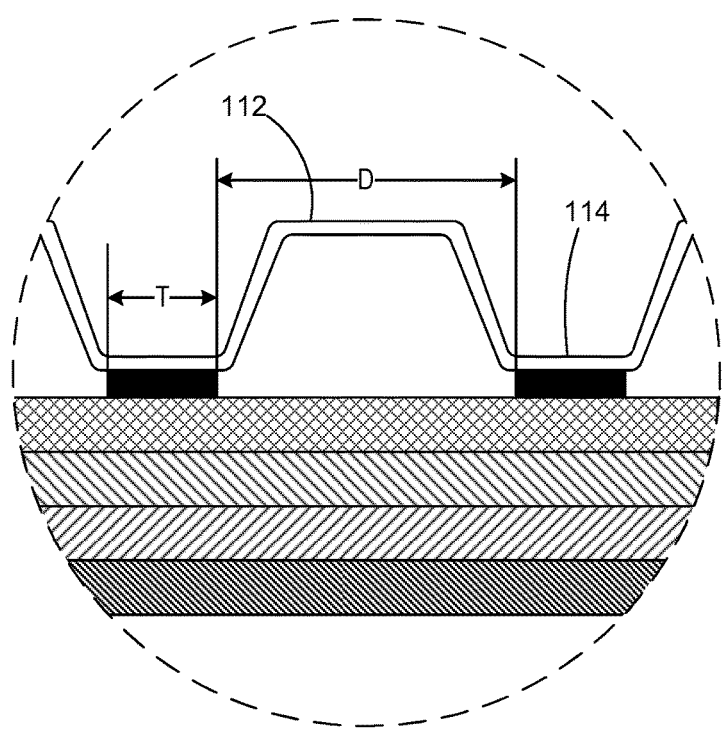
FIG. 4 is an enlarged cross-sectional view of the absorbent article illustrating the multiple peaks and valleys of the first layer or top sheet created by the glue/adhesive pattern coupling the first layer and the second layer together.

The top sheet 110 and absorbent core 120 are joined together via a plurality of adhesive bonds or beads 116. The plurality of adhesive beads 116 may be arranged in a parallel pattern relative to one another along a length of the top sheet 110 and absorbent core 120, as shown in FIGS. 1 and 2, for example. The particular adhesive bead layout results in a plurality of longitudinal peaks 112 and valleys 114 that are adjacent and substantially parallel to one another and extend along the length of the top sheet 110, which is shown in greater detail in FIGS. 3 and 4. In particular, as shown in FIGS. 3 and 4, the valleys 114 are formed via the plurality of adhesive beads 116 coupling the top sheet 110 and absorbent core 120 to one another. As shown in FIG. 4, for example, each adhesive bead 116 may have a thickness T of approximately 1 mm, for example and may be spaced apart from an immediately adjacent adhesive bead 116 by a distance D, which may be approximately between 1 mm and 5 mm, for example. Accordingly, the plurality of longitudinal peaks 112 and valleys 114 are generally formed as a result of the particular adhesive bead pattern.

It should be noted that, in other embodiments, the peaks and valleys may be arranged in a various patterns and need not be limited to a longitudinal pattern. For example, in some embodiments, the peaks and valleys may be oriented in a substantially horizontal direction or a substantially diagonal direction relative to the first and second layers. Yet still, in some embodiments, different portions of the first layer may include different patterns of peaks and valleys, such that the pattern of peaks and valleys can vary throughout the entire area of the first layer. For example, some sets of peaks and valleys may extend in a first direction and other sets of peaks and valleys may extend in a second direction different than the first direction (e.g., first set oriented in a longitudinal direction parallel with length of article and second set oriented in a horizontal direction parallel with width of article). Furthermore, in some embodiments, the peaks and valleys may be intermittently formed along the first layer in such a manner that they are not continuous.

The plurality of longitudinal peaks and valleys may be configured to improve at least one of: softness, rate of acquisition (ROA), efficiency of use of absorbent surface area (which can provide significant cost savings), wicking direction of fluid flow (which can be useful in reducing leakage from the article), and a combination thereof.

The peaks 112 and valleys 114 may result in improvement to at least one of softness, rate of acquisition (ROA), efficiency of use of absorbent surface area (which can provide significant cost savings), wicking direction of fluid flow (which can be useful in reducing leakage from the article), and a combination thereof, thereby improving performance of the underpad 100.

The top sheet 110 is configured to be direct contact with a person's skin and thus is desired to be very soft. The softer the material, the more comfortable it is to the human skin. This is especially needed for bedridden patients, who lie on top of the underpad for long periods of time. It is also desirable that the top sheet 110 be resilient, providing a cushion on top of the absorbent core 120. The absorbent core 120 may be a little stiff, especially when using airlaid composites. The absorbent core 120 may also contain loose SAP particles, when using combined pulp/superabsorbent polymer (SAP) materials. The SAP particles could irritate the skin, when in direct contact. In order to overcome these potential issues, the top sheet 110 has a relatively higher basis weight than current underpad designs. For example, the top sheet 110 has a basis weight in the range of approximately 15 gsm to 45 gsm. The top sheet 110 having a basis weight in this range can help insulate the skin against irritating materials and stiff composites, particularly when in the dry state.

The higher basis weight of the top sheet 110 can also help insulate the skin against fluid rewet or SAP gel migration, when in the wet state. This is especially true for an absorbent core 120 containing high levels of pulp and/or no tissue. Pulp fibers may offer very little fluid retention. While adding more SAP materials may improve fluid retention, the addition of SAP materials may increase the potential for SAP migration. A thinner or lower basis weight top sheet, as is found in current underpads, may allow free fluid and/or SAP gel to bleed-through it, especially under pressure. This is particularly troublesome, considering most persons utilizing underpads are lying directly on top of the product for prolonged periods, resulting in the product undergoing constant and high levels of stress.

The higher basis weight of the top sheet 110 is able to increase the retention capacity of the underpad 100, especially at high SAP weights and no tissue wrapping of the absorbent core 120. Furthermore, the higher basis weight of the top sheet 110 can also provide improved durability and tensile strength. Durability and strength is a particularly important characteristic for the top sheet 110, as it is crucial that the top sheet 110 does not rip or tear during use, especially under constant stress and shear. Furthermore, the tensile strength is an additional feature that is important for ensuring that the underpad 110 can be used to lift and transport/reposition a person. The top sheet 110 has a tensile strength, when measured by ASTM D 882 method, in the range of approximately 25 N/25 to 80 N/25 mm in the machine direction and approximately 9 N/25 to 50 N/25 mm in the cross direction.

The higher basis weight of the top sheet 110 further provides for a faster rate of acquisition (ROA), especially since the absorbent core 120 may be relatively thin and there is no acquisition layer in the present underpad 100. Thus, due to the thicker or higher basis weight, the top sheet 110 generally acts a combined top sheet and acquisition layer, which results in absorbing liquid at a faster rate.

The higher basis weight for the top sheet 110 further provides for an underpad 100 with reduced pressure points against a person's body, which is especially important for patients who are bed-ridden or immobilized and prone to enduring irritation and/or formation of skin ulcers.

Accordingly, the top sheet 110 of the underpad 100, specifically the higher basis weight in the range of 15 gsm to 45 gsm, provides numerous advantages over current underpad designs, including, but not limited improved softness and resiliency for skin wellness, faster ROA for thin absorbent substrates, improved insulation against SAP particle migration and stiff absorbent cores in the dry state, improved insulation against free fluid and SAP gel migration in the wet state, and increased tensile strength to improve material durability and provide additional feature to lift heavy loads.

In some embodiments, the top sheet 110 includes at least one of a nonwoven material, a hydrophilic or partially hydrophilic material, a nonwoven material with a zone-coated surfactant, and a nonwoven and apertured film. One material that can be used for the top sheet is a 22 gsm SBPP (Spunbond Polypropylene) hydrophilic nonwoven, commercially available from Avgol, located in Tel Aviv, Israel. The surfactant on the top sheet 110 can be zone-coated, for example, which may provide a barrier along particular portions (e.g., the sides) of the underpad 100 to reduce fluid leakage.

The absorbent core 120 may generally include an absorbent material, a nonabsorbent material, and a combination thereof. For example, the absorbent core 120 may include one or more of: "pulp only" core; "pulp & SAP" core; "pulp & SAP & tissue" core; "airlaid composite" core; "airlaid composite" core with cotton fibers; "rayon viscose" core; "rayon viscose & pulp" core; "rayon viscose & SAP" core; "rayon viscose & pulp & SAP" core; "rayon viscose & pulp & SAP & tissue" core; "tissue" core; "tissue & SAP" core; "creped tissue or paper towel" core; "creped tissue with SAP" core; "pulp & curly fiber" core; "pulp & curly fiber & SAP" core; and "pulp & curly fiber & SAP & tissue" core.

The pulp in the absorbent core 120 may have odor control and/or pH control and/or anti-bacterial properties. One material that can be used for pulp is Golden Isle CO Fluff (Grade 4855) available from Georgia Pacific, located in Atlanta, Ga. This pulp is capable of neutralizing ammonia odors. Similarly, the SAP in the absorbent core 120 may have odor control and/or pH control and/or anti-bacterial properties. One material that can be used for SAP is FAVOR SXM 7900 available from Evonik, located in Greensboro, N.C.

The fluid impervious barrier 130 may be breathable in some embodiments, while in other embodiments, the barrier 130 is not breathable. Additionally, the barrier 130 can be cloth-like or non-cloth-like. For example, a cloth-like material for the barrier 130 a Poly Laminate, from Berry Plastics located in Chippewa Falls, Wis. One poly film that can be used for the barrier 130 is a polyethylene/polypropylene film blend available from Berry Plastics located in Chippewa Falls, Wis. One breathable poly film that can be used for the barrier 130 is a micro-porous film available from Clopay located in Mason, Ohio. One breathable cloth-like material for the barrier 130 that can be used is Poly Laminate available from Galaxy, China.

The fourth layer 140 may generally be referred to herein as the "back sheet 140", as it generally includes a nonwoven material configured to cover the barrier 130. Generally, the back sheet 140 is unnecessary when the barrier 130 includes a poly laminate (which already contains nonwoven material).

In some embodiments, it may be beneficial to laminate the barrier 130 to the back sheet 140 directly on the manufacturing machine, for economic reasons. The lamination could be achieved through ultrasonic bonding, adhesive application, heat sealing, etc. or a combination of different bonding techniques.

Yet further still, the underpad 100 may include a fifth layer 150, as previously described herein. The fifth layer 150 may include a fastening means for attaching the entire underpad 100 to an object, such as a garment, bed linens, chair, so as to prevent unwanted movement of the underpad. The fastening means may include micro-hooks which could attach to the woven fibers on the bed sheet, for example. One suitable micro-hook would be Microplast Mushroom/Hexagonal Hook-Article 85445 (Blue), available from Gottlieb Binder GmbH located in Holzgerlingen, Germany. The advantage of this micro-hook is that it can attach itself to fibers in any direction and is made of polypropylene and is approximately 0.3 mm in thickness.

Another means of attachment may comprise of pressure-sensitive adhesive and release paper (as currently used on sanitary napkins). It would be placed on the backside of the underpad. The release paper would be removed from the underpad, exposing the pressure-sensitive adhesive, and then the underpad would be adhered to the bed sheet or other non-fibrous surface. One suitable Positioning Adhesive is NW-1043 available from H.B. Fuller located in Vadnais Heights, Minn. One suitable Release Paper is MGA D3H/ 040 mm (32 gsm) available from Mondi Gronau GmbH located in Gronau, Germany.

It should be noted that the attachment/fastening mechanisms described herein may be used for attaching the layers of the underpad 100 to one another in some instances.

Various characteristics of underpad 100 consistent with the present disclosure were tested, including testing of run-off properties of the underpad 100.

Table 1 below is a general procedure for the Run-Off test, which is generally guided by the Run-Off Test Method provided by INDA's WSP Standard 80.9 R4 (12).

TABLE 1

| Setting | Modifications | INDA Standard | Comment |
|---|---|---|---|
| Angle | 30° | 25° | Used 30 degrees (instead of 25 degrees) to better simulate a 30 degree bed angle, which is the worst case scenario. |
| Fluid units | Milliliter | Grams | Standard calls for weighing 25 grams, whereas volume was used instead. At 0.9% saline, the density is so close to water that the conversion from milliliters to grams is insignificant. |
| Rate/Speed | 25 ml over 6.5 sec | 25 g over 4 sec | A separatory funnel was used which had a slightly slower flow-rate versus the standard. This will impact results slightly as well. |
| Teste Media | Fully constructed pad | Test nonwoven over standard filter paper | Testing involved the overall underpad, not just the nonwoven. Thus, filter paper was not necessary. |
| Clips | Paper clips | None | Paper dips were used to flatten-out the Underpad, which had some creases due to folding. |

The procedure for the Run-Off Test Method is provided in outline form below:
1.1.1 Apparatus
  30 degree stand
  Separatory funnel with stopcock
  Syringe
  Plastic clipboard
  Plastic plate/tray
  Weight scale-gauge #0856
  Protractor
1.1.2 Procedure
  The fixture is set up with a flat surface at 30°.
  The funnel dispenser is set up in the vertical position such that the liquid from the funnel when released drops directly on the sample.
  The sample is aligned and secured on the flat plane with paper clips such that the leading edge is 3 mm off the end of the flat plane.
  The plastic plate is placed on the weighing scale. Zero the weighing scale
  The plastic plate is placed at the end of the flat surface.
  With the syringe 25 ml of saline solution is drawn and dispensed into the funnel.
  The stopcock is turned to release the saline on to the pad.
  The plastic tray is placed on the weigh scale. Record the data.
  Table 2 below provides test results from the Run-Off Test (inclined at 30 degrees) of underpad samples having different basis weights.

TABLE 2

Run-Off Test Results of Underpad Samples

| Underpad Sample | Top Sheet Basis Weight | Adhesive Bead Shim | Run-Off (MD) | Run-Off (CD) |
|---|---|---|---|---|
| Sample 1 | 10 gsm | 1 mm × 1 mm | 9.6 g | 7.9 g |
| Sample 2 | 15 gsm | 1 mm × 4 mm | 3.1 g | 2.0 g |
| Sample 3 | 17 gsm | 1 mm × 4 mm | 2.5 g | 1.6 g |

According to the results of Table 2, the increase in basis weight of the top sheet results in significant decrease in liquid run-off in both directions (machine direction and cross direction). The improvements to run-off is a result of higher basis weight (gsm) of the top sheet and wider, spaced-out, adhesive beads on the top sheet of the underpad (as a result of the 1 mm×4 mm pattern), thereby manipulating the peaks and valleys (e.g., spacing out the distance between adjacent valleys).

A standard underpad sample (underpad having a top sheet of 10 gsm) and at least one underpad consistent with the present disclosure were further subjected to ROA and rewet testing to determine ROA and rewet values. The procedure for the ROA and Rewet Test Method is provided in outline form below.
1. Purpose:
  To determine the amount of time required for the absorbent article to absorb, accept and retain a fixed amount of 0.9% saline solution.
2. Scope:
  Briefs, Underwear, Underpads, Liners, Training pants, Baby Diapers
3. Equipment Needed:
  3.1. 0.9% saline solution
  3.2. Seperatory funnel discharging at 7 ml/sec
  3.3. Seperatory funnel holder or stand
  3.4. Timer
  3.5. Stop Watch
  3.6. Round stainless steel cylinder weighing 9.8 lbs
  3.7. Dosing tube with 4"×4"×0.5" 2.2 LB weighted base. Tube height 9", tube inside diameter 1"
  3.8. 250 ml graduated cylinder
  3.9. VWR grade 950.9 cm filter papers
  3.10. Analytical scale able to weigh to the nearest 0.1 grams
4. Method:
  4.1. Verify equipment used is within its calibration date.
  4.2. Fluid Dosage:
    4.2.1. Brief: Youth and small sizes use a single dose of 100 ml of 0.9% saline solution.
    4.2.2. Brief: Medium-bariatric sizes use a single dose of 200 ml of 0.9% saline solution.
    4.2.3. Adult protective underwear use a single dose of 100 ml of 9% saline solution.
    4.2.4. Under pad use a single dose of 100 ml of 0.9% saline solution.
    4.2.5. Liner use a single dose of 100 ml of 0.9% saline solution.
    4.2.6. Baby Diapers: New Born Diapers use a single dose of 40 ml of 0.9% saline solution.

4.2.7. Baby Diapers: Size 1 & 2 use a single dose of 60 ml of 0.9% saline solution 4.2.8. Baby Diapers: Size 3 use a single dose of 80 ml of 0.9% saline solution 4.2.9. Baby Diapers: Size 4-6, Training Pants and Youth Pants: use a single dose of 100 ml of 0.9% saline solution 4.3. Sample Preparation:

4.3.1. Cloth back products: lay the product flat pad side up on the workbench using hook tape to hold the product down and in place.

4.3.2. Poly back products: Cut all elastics so that the product is laid flat on the workbench.

4.3.3. Protective underwear: lay the product flat pad side up on the workbench using hook tape to hold the product down and in place.

4.3.4. Under pad: lay the under pad flat on the workbench pad side up.

4.3.5. Liner: lay the liner flat on the workbench pad side up, if the product has a poly backing and elastics the elastics will need to be cut in a way that the product lays flat.

4.4. Sample Testing:

4.4.1. Weigh and record the product weight on to the appropriate form.

4.4.2. Using the graduated cylinder measure the needed amount of 0.9% saline solution for the product being tested.

4.4.3. Place the dosing tub in the center of the product pad.

4.4.4. Place funnel stand and funnel directly over the dosing tub in the center of the product.

4.4.5. Pour the 0.9% saline solution into the seperatory funnel, as soon as the liquid starts to drop from the funnel start the stopwatch.

4.4.6. Stop the stopwatch when all the liquid has passed into the product and no longer puddles in the dosing tub.

4.4.7. Start a 12 minute timer.

4.4.8. Record the ROA on the appropriate form. Report ROA time in seconds.

4.4.9. When the 12 minute timer goes off re-set the timer for 1 minute.

4.4.10. Weigh a stack of filter papers and record the weight on the top filter paper. The dry weight of the filter paper should be 10.0 grams (+/−1 gram). Place the stack of filter papers on the center of the insult point.

4.4.11. Gently place the cylindrical weight on top of the dry filter papers.

4.4.12. Start the 1 minute timer.

4.4.13. When the timer goes off remove the weight from the filter papers.

4.4.14. Remove the filter papers from the product and place on scale.

4.4.15. Subtract the dry weight of the filter papers from the wet weight of the filter papers.

4.4.16. Record the difference in filter paper weight (rewet) on the appropriate form.

Table 3 below provides test results from the ROA and Rewet Test Methods of underpad samples having different basis weights.

TABLE 3

ROA and Rewet Test Results of Underpad Samples

| Underpad Sample | Top Sheet Basis Weight | Adhesive Bead Shim | ROA | Rewet (grams) |
|---|---|---|---|---|
| Sample 1 | 10 gsm | 1 mm × 1 mm | 204 sec | 4.5 g |
| Sample 2 | 17 gsm | 1 mm × 4 mm | 171 sec | 2.7 g |

Figure 5:
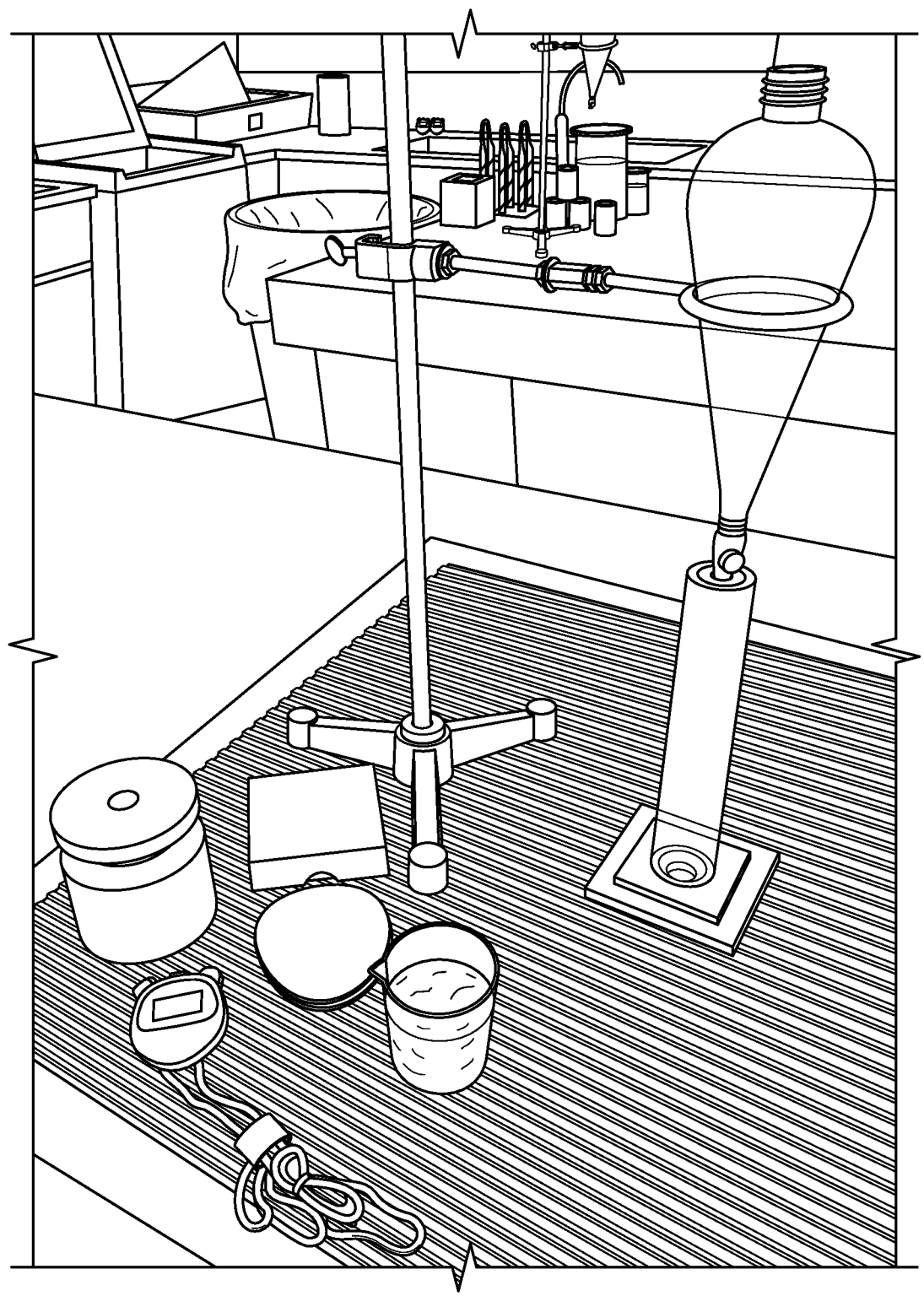
FIG. 5 illustrates a rate of acquisition (ROA) and rewet testing setup for testing the absorbency characteristics of the disposable absorbent article of the present disclosure.
Figure 6A:
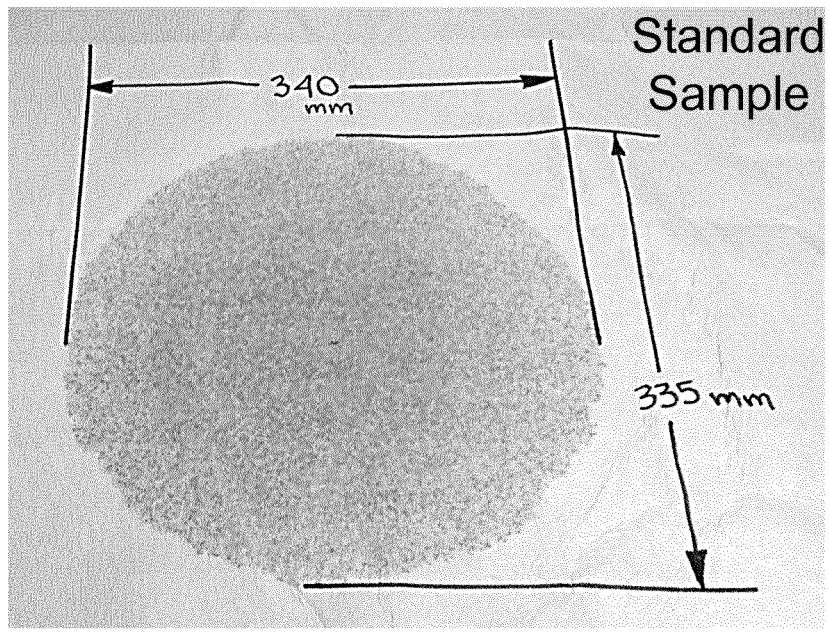
FIGS. 6A and 6B illustrate test results for the ROA and rewet testing of the absorbent article of the present disclosure.
Figure 6B:
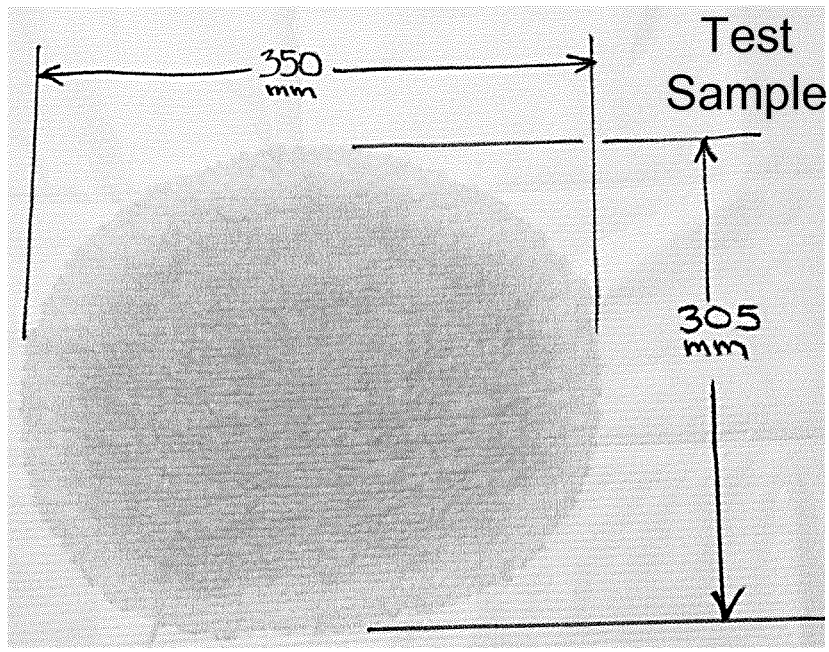

FIG. 5 illustrates a rate of acquisition (ROA) and rewet testing methods setup for testing the absorbency characteristics of a standard underpad and underpad 100, according to the ROA and Rewet Testing Method described above. FIGS. 6A and 6B illustrate test results for the Run-Off, ROA, and rewet testing of a standard underpad and an underpad consistent with the present disclosure. In particular, FIG. 6A is a photograph of test results of a standard underpad (Sample 1 from Table 3), including a top sheet having a basis weight of approximately 10 gsm, an Airlaid absorbent core having a basis weight of approximately 135 gsm, and an adhesive shim pattern of 1 mm×1 mm. FIG. 6B is a photograph of test results of an underpad consistent with the present disclosure (Sample 2 from Table 3), including a top sheet having a basis weight of approximately 17 gsm, an Airlaid absorbent core having a basis weight of approximately 175 gsm, and an adhesive shim pattern of 1 mm×4 mm.

According to the results of Table 3, the ROA and Rewet values of Sample 2 are lower than the ROA and Rewet values of Sample 1. In particular, the particular design of Sample 2 resulted in approximately a 16% decrease in ROA and approximately a 40% decrease in Rewet, wherein, generally, the lower the values for ROA and Rewet, the better the underpad for a consumer. Accordingly, the increase in basis weight of the top sheet of Sample 2 from 10 gsm to 15 gsm, as well as the different adhesive shim pattern (a 1 mm×4 mm pattern in contrast to a 1 mm×1 mm pattern), results in improved ROA and Rewetting values for Sample 2 when compared to Sample 1, specifically a faster ROA of liquid absorbed into the underpad, and a lower rewet (liquid resurfacing through top sheet under pressure). Furthermore, as previously described herein, increasing the basis weight of the top sheet and including a 1 mm×4 mm adhesive shim pattern further improved run-off. These improvements are especially significant when using Airlaid or Tissue with SAP absorbent cores in an underpad.

Furthermore, as shown in FIGS. 6A and 6B, the basis weight of the top sheet as well as the adhesive shim pattern results in a particular fluid distribution pattern. For example, the standard underpad (Sample 1 of Table 3) of FIG. 6A has a more round-shaped fluid distribution pattern, having a width of approximately 340 mm and a length of approximately 335 mm, which can be attributed to the adhesive shim pattern being 1 mm×1 mm. In contrast, the test underpad (Sample 2 of Table 3) of FIG. 6B has a more oval-shaped fluid distribution pattern, having a width of approximately 350 mm and a length of approximately 305 mm, which can be attributed to the adhesive shim pattern being 1 mm×4 mm. In particular, as a result of having an adhesive shim pattern of 1 mm×4 mm, resulting wider, spaced-out, adhesive beads on the top sheet of the underpad and thus peaks and valleys correspondingly arranged. The peaks and valleys are able to increase fluid distribution in a longitudinal direction following the length of the peaks and valleys, thereby resulting in a more oval-shaped fluid distribution pattern, which can be particularly advantageous when providing underpads that have a rectangular shape.

For example, the adhesive shim pattern can be useful in creating channels (peaks and valleys) extending in a desired direction, such as extending in a direction substantially parallel to the length of the rectangular underpad (shown in FIG. 1), which, in turn, will result in fluid distribution in such a direction. Thus, the channel pattern can be useful in spreading the fluid in a desired direction much more efficiently, so as to reduce the total coverage area of a product, which can save costs. Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

The invention claimed is:

1. An absorbent article for placement upon a bed sheet, the absorbent article comprising:
    a first layer configured to engage a subject's skin, the first layer comprising a breathable and fluid permeable material configured to absorb fluid and provide a degree of compression against the subject's skin;
    at least a second layer coupled to the first layer via a plurality of adhesive bonds, the second layer comprising an absorbent material for absorbing a fluid passing through the first layer, wherein the first and second layers are each rectangular in shape; and
    a plurality of micro-hooks beneath the first and second layers and configured to releasably attach the absorbent article to the bed sheet;
    wherein the first layer comprises a plurality of longitudinal peaks and valleys adjacent to one another and extending linearly along a length of the first layer all the way to at least one edge of the absorbent material, wherein the peaks and valleys are formed via the plurality of adhesive bonds coupling the first and second layers to one another;
    wherein the plurality of peaks and valleys are configured to distribute fluid along the first layer and into the second layer in a direction corresponding to the orientation of the peaks and valleys.

2. The absorbent article of claim 1, wherein the plurality of adhesive bonds are arranged in a substantially parallel pattern relative to one another along a length of the first and second layers such that the plurality of peaks and valleys are substantially parallel to one another.

3. The absorbent article of claim 1, wherein the plurality of peaks and valleys are configured to distribute fluid along the first layer and into the second layer in a substantially longitudinal direction corresponding to the longitudinal orientation of the peaks and valleys.

4. The absorbent article of claim 1, wherein each of the plurality of adhesive bonds is positioned from an immediately adjacent adhesive bond in the range of approximately 1 mm to 10 mm such that the plurality of peaks are spaced apart from one another via each valley; preferably in the range of approximately 3 mm to 5 mm; more preferably by 4 mm.

5. The absorbent article of claim 1, wherein each adhesive bond extends an entire length of the first and second layers.

6. The absorbent article of claim 1, wherein some of the adhesive bonds extend along a portion of the length of the first and second layers.

7. The absorbent article of claim 1, wherein at least one of the adhesive bonds is intermittently disposed between the first and second layers.

8. The absorbent article of claim 1, wherein the plurality of longitudinal peaks and valleys improves at least one of surface area of the first layer, softness of the first layer, rate of acquisition (ROA) of the first layer, and a combination thereof.

9. The absorbent article of claim 1, wherein the first layer comprises a nonwoven material including hydrophilic or partially hydrophilic material and having a zone-coated surfactant.

10. The absorbent article of claim 1, wherein the first layer comprises a nonwoven and apertured film.

11. The absorbent article of claim 1, wherein the absorbent article has a rate of acquisition (ROA) in the range of approximately 50 to 200 seconds; and/or wherein the absorbent article has a rewet in the range of approximately 0.1 grams and 10.0 grams; and/or wherein the breathability is measured as moisture vapor transmission rate (MVTR) having a metric perm value in the range of approximately 400 g/sm/day to 10,000 g/sm/day.

12. The absorbent article of claim 1, wherein the second layer comprises a nonabsorbent material combined with the absorbent material; wherein preferably the second layer comprises cellulose selected from the group consisting of wood fibers, plant fibers, cotton fibers, fluff pulp and viscose rayon; wherein preferably the fluff pulp provides at least one of odor control, anti-bacterial properties, pH control, and a combination thereof.

13. The absorbent article of claim 1, wherein the absorbent material of the second layer comprises a superabsorbent polymer; wherein preferably the superabsorbent polymer comprises of a polymer or copolymer of sodium polyacrylate; wherein preferably the superabsorbent polymer provides at least one of odor control, anti-bacterial properties, pH control, and a combination thereof.

14. The absorbent article of claim 1, wherein the absorbent material of the second layer comprises any one of the following: tissue, an airlaid composite, a pulpless absorbent material.

15. The absorbent article of claim 1, wherein the first layer has a basis weight in the range of approximately 15 gsm to 45 gsm.

16. The absorbent article of claim 1, further comprising a third layer coupled to the second layer and separated from the first layer via at least the second layer, the third layer comprising at least a fluid impervious material.

17. The absorbent article of claim 16, wherein the third layer comprises any one of the following: a breathable micro-porous poly film, a breathable SMS (Spunbond/Meltblown/Spunbond) nonwoven material, wherein optionally the SMS nonwoven material has a slot coated adhesive.

18. The absorbent article of claim 1, wherein the first layer has:
- a basis weight in the range of approximately 15 gsm to 45 gsm; and
- a tensile strength, when measured by ASTM D 882 method, in the range of approximately 25 N/25 to 80 N/25 mm in the machine direction and approximately 9 N/25 to 50 N/25 mm in the cross direction; and further comprising:
- a third layer coupled to the second layer and separated from the first layer via at least the second layer, the third layer comprising at least a fluid impervious material.

19. The absorbent article of claim 1, wherein each of the plurality of adhesive bonds is positioned from an immediately adjacent adhesive bond in the range of approximately 1 mm to 4 mm such that the plurality of peaks are spaced apart from one another via each valley.

* * * * *